United States Patent [19]

Rosenthal

[11] Patent Number: 4,990,772
[45] Date of Patent: * Feb. 5, 1991

[54] APPARATUS AND METHOD FOR CALIBRATING A NEAR-INFRARED INTERACTANCE PROBE

[75] Inventor: Robert D. Rosenthal, Gaithersburg, Md.

[73] Assignee: Futrex, Inc., Gaithersburg, Md.

[*] Notice: The portion of the term of this patent subsequent to Dec. 30, 2003 has been disclaimed.

[21] Appl. No.: 507,542

[22] Filed: Apr. 11, 1990

Related U.S. Application Data

[63] Continuation of Ser. No. 252,548, Oct. 3, 1988, Pat. No. 4,928,014.

[51] Int. Cl.$^5$ .............................................. G01N 21/55
[52] U.S. Cl. ................................. 250/252.1; 250/341; 250/358.1
[58] Field of Search .............. 250/341, 252.1 A, 358.1

[56] References Cited

U.S. PATENT DOCUMENTS 4,801,804  1/1989  Rosenthal .......................... 250/339

FOREIGN PATENT DOCUMENTS 823832  11/1959  United Kingdom ................ 356/243

Primary Examiner—Carolyn E. Fields
Attorney, Agent, or Firm—Bernard, Rothwell & Brown

[57] ABSTRACT

A probe for near-infrared interactance quantitative analysis is calibrated by placing the near-infrared source and detector within a cavity of a calibrating sleeve. The cavity provides a reflectance value that corresponds to an interactance calibration value for which the probe is being calibrated.

2 Claims, 2 Drawing Sheets

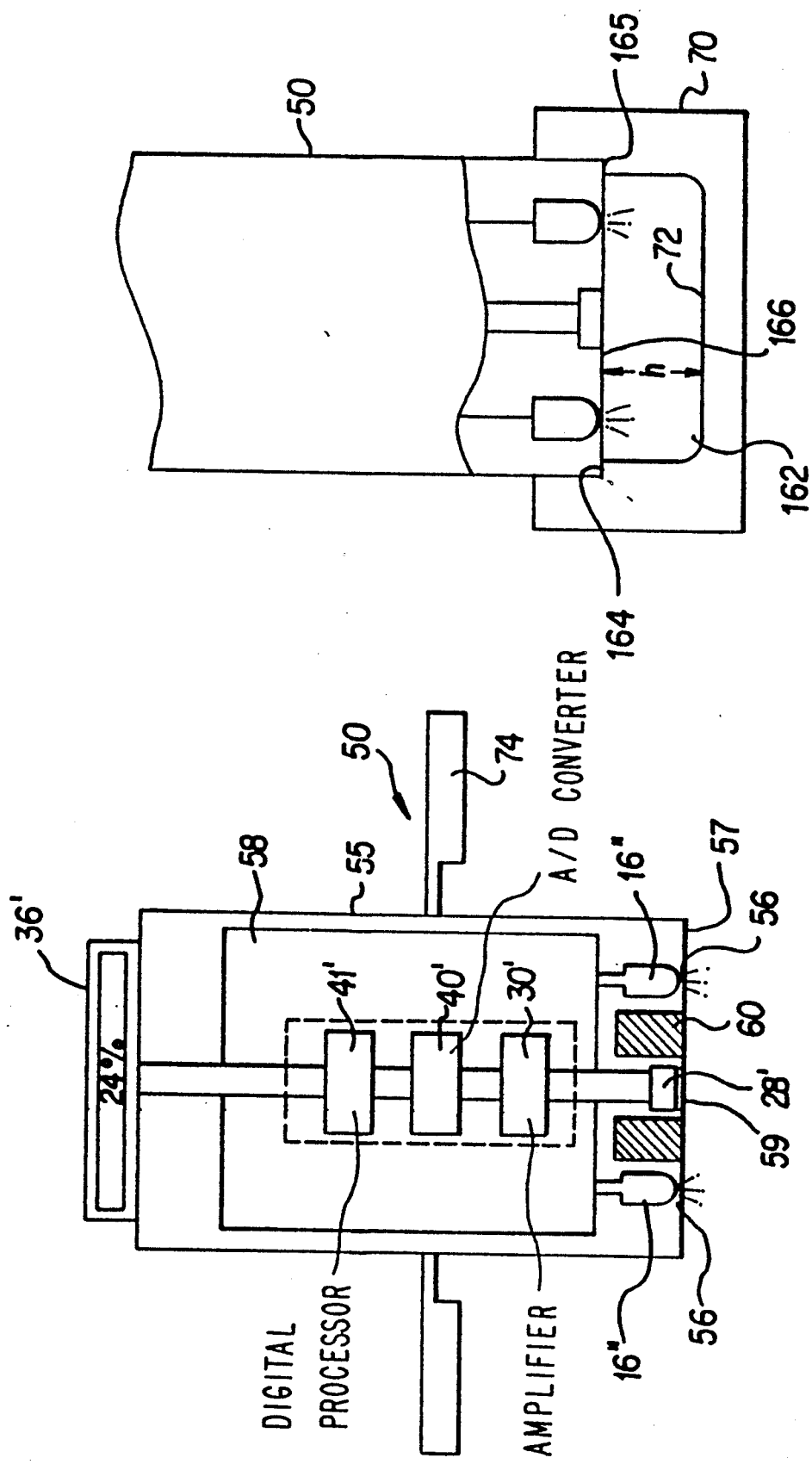

APPARATUS AND METHOD FOR CALIBRATING A NEAR-INFRARED INTERACTANCE PROBE

This is a continuation of application Ser. No. 252,548 filed Oct. 3, 1988 now U.S. Pat. No. 4,928,014.

BACKGROUND OF THE INVENTION

1. Field of the Invention

The present invention relates to improvements in instruments and methods for performing near infrared quantitative analysis to determine percent fat in a body.

2. Description of the Background Art

It has long been known that obesity reduces longevity, and recent studies have demonstrated that high percentage of body fat is an independent health risk factor as a cause of heart attack, stroke, diabetes and other disabling diseases. (Stokes et al, *Metabolic Complications of Human Obesities;* Elsevier Science Publishers, B.V. (Biomedical Division); J. Vague et al, eds.; pp. 49–57 [1985]).

For the above reasons, several techniques have been developed to determine percent body fat, including recent techniques based on U.S.A. research that demonstrates that "near-infrared light interactance" can provide the basis for measurement of percent body fat (Conway et al, *The American Journal of Clinical Nutrition* 40:1123–1130 [1984]).

Near-infrared light interactance technology disclosed in U.S. Pat. No. 4,633,087 to Rosenthal et al has recently been utilized in a commercial instrument for measurement of body composition, i.e., percent fat in the human body. However, because of the cost required to manufacture an instrument that utilizes this technology, the majority of purchasers are health clubs, medical centers and sports teams, with only a very small percentage of buyers being individual consumers.

Taking full advantage of the technology disclosed in U.S. Pat. No. 4,633,087 requires the measurement of more than one wavelength in the near-infrared spectrum. The reason for this is that what is being measured is the change in slope of the absorption curve, with the slope being defined as the difference in optical absorption at two defined wavelengths.

For the following reasons, the cost of utilizing the technology described in U.S. Pat. No. 4,633,087 remains high even when utilizing inexpensive infrared emitting diodes (IREDs) as the near-infrared source:

(1) The use of two IREDs are preferred for each of two wavelengths being measured, and the more IREDs that are used, the greater the expense.

(2) An electronic means for turning on and off each pair of IREDs in a sequential fashion and keeping them on for a predetermined length of time is required.

(3) Circuitry is required that allows the output of the pairs of IREDs to be adjusted so that they have equal energies when measuring a neutral sample.

(4) Computation circuitry is required that must not only discriminate between two pairs of IREDs, but also perform a multiple regression calculation.

(5) Instrument display capability is required that has the ability to read-out each of the two pairs of IREDs well as the final percent fat.

(6) The instrument must also have the ability of entering a multiple number of constants because of the multiterm linear regression equation utilized.

In addition to each of the items discussed above, a major element in the production cost of current near-infrared analysis instruments is the need to calibrate each production unit against a series of known samples via multiple linear regression analyses. These calibration steps are labor intensive and their elimination would enable great reductions in the cost of producing such instruments.

In view of the costs required in providing known devices for measuring body fat content, there remains a need in the art for improved and less expensive devices for measuring percent body fat.

SUMMARY OF THE INVENTION

In accordance with the present invention, a method for determining percent fat in a body comprises placing a point source of near-infrared radiation against a body, transmitting near-infrared radiation into the body, detecting near-infrared radiation which interacted with the body and providing a readout, based on near-infrared absorption by the body during interactance, indicative of body fat content. Placing the point source against the body eliminates the need for the light-diffusing probes of the prior art.

The invention further related to apparatus for quantitatively measuring fat content of a body comprising at least one point source means of near-infrared radiation, a near-infrared detector capable of providing an electrical signal upon detection of near-infrared radiation, and means for placing the point source means against the body so as to introduce near-infrared radiation for absorption measurement. Data on a plurality of physical parameters, especially height and weight, may be utilized along with the measured absorption to quantitatively determine fat content.

BRIEF DESCRIPTION OF THE DRAWINGS

FIG. 1 is a sectional, partially schematic view of an instrument according to an embodiment of the present invention.

FIG. 2 is a sectional, partially schematic view of the instrument of FIG. 1 in combination with a calibration sleeve.

DETAILED DESCRIPTION OF THE PREFERRED EMBODIMENTS

Figure 3:
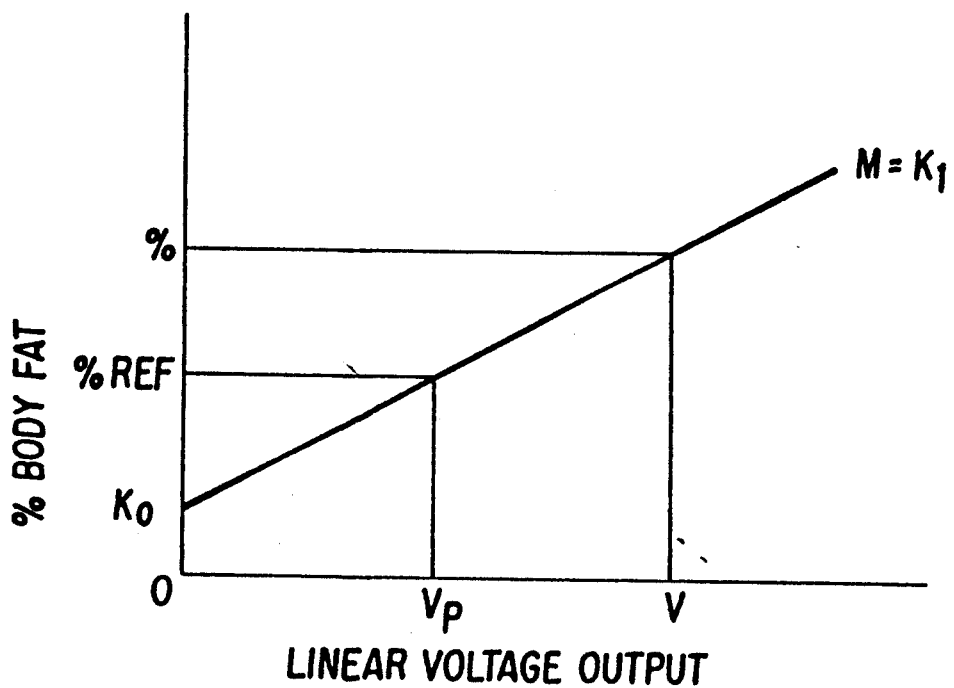
FIG. 3 is a plot of linear voltage output from an optical detector versus percent body fat of a subject.

The invention provides method and apparatus for determining percent body fat utilizing optical interactance principles in the near-infrared radiation wavelength range of from about 740 to about 1100 nanometers. Because of the relationship between optical density (O.D.) and percent body fat, O.D. measurement of a single bandwidth of near-infrared radiation can be utilized to provide a high correlation with percent body fat.

Optical density ordinarily is defined as log 1/I, wherein I is interactance and equal to $E_S/E_r$ ($E_s$ = energy received from subject; $E_r$ = energy received from a reference). An important aspect of the present invention is the substitution of much simpler 1/I mathematics for the conventional log (1/I) mathematics. When taking a measurement halfway between the shoulder and elbow on the biceps of a person's prominent arm (the one used for writing), the local amount of fat measured is directly proportional to the total fat in the body. With the present invention, a single bandwidth measurement can provide meaningful measurement of percent total body fat. A single bandwidth is able to provide this measurement since the higher the percent body fat, the more transparent the arm of the subject. This is because low body fat people have "hard muscles" that make it difficult for light to penetrate, therefore providing high O.D. values. Conversely, people with high percent body fat have a "flabby" biceps that is not very optically dense, resulting in low O.D. values.

Although there is no need to be particularly specific in the bandwidth of interest that the IRED emits, so long as it is within the near-infrared spectrum, the larger the half-power bandwidth of the light source, within reason, the better the measurement, since less interference from other body parameters occurs. Thus, the use of a conventional 950 nanometer IRED as the illumination source is almost ideal. Such infrared-emitting diodes have half-power bandwidths of almost 60 nanometers, which make them practically immune to other types of absorptions (e.g., absorption due to moisture, protein, etc.).

This invention utilizes the principal of interactance, which principle is known in the art and differs from reflectance and transmittance. In interactance, light from a source is shielded by an opaque member from a detector and interactance of the light with the test subject is then detected by the detector.

Since the present invention measures radiation of only a single near-IR bandwidth (which may be emitted from only a single IRED), there is no need for the instrument to cycle on and off, as is required when utilizing multiple bandwidth measurements. Thus, there is no need for the inclusion of a timing circuitry nor IRED cycling circuitry, as is provided in a multiple bandwidth instrument.

An instrument in accordance with a preferred embodiment of the invention is illustrated in FIG. 1. In this embodiment, a light transmitting and diffusing member as taught in connection with many prior devices is not needed. Instead, at least one and preferably a pair of IREDs and an optical detector are positioned within the instrument for placement directly adjacent to the skin of the subject, with substantially no loss of fat measuring accuracy.

The instrument 50 is dimensioned for hand-held operation and includes a case 55 housing one or more IREDs 16", a pair of which are shown in opposite sides of the lower portion thereof. When more than one IRED is employed, they should be of about the same bandwidth and center frequency output. The IREDs are disposed opposite window openings 56 in a bottom surface 57 of the case 55. The windows 56 may further include near-infrared-transparent coverings (not shown) to prevent the entry of dust and dirt into the instrument.

An optical detector 28', also positioned in the lower portion of the case 55, is substantially equidistant from each IRED 16". The detector 28" is disposed within a window opening 59 which, like the windows for the IREDs, may include a covering transparent to near-IR radiation. If desired, the window covering over detector 28" can be electronically conductive to provide EMI shielding. Light baffles 60 are placed between each IRED 16" and the detector 28 to prevent erroneous readings caused by direct impingement of near-IR radiation onto the detector. The baffles 60 are constructed of any opaque and preferably lightweight material. Erroneous readings also are prevented by the provision of a flexible light shield 74 which blocks ambient light from impinging upon the detector.

The detector 28' and each of the IREDs 16" are mounted within the case 55 on a printed circuit (PC) board 58 which also serves as a carrier for the remainder of the electronic components.

The optical detector 28' is connected to the input of an electrical signal amplifier 30' which in turns feeds the amplified signal to an analog-to-digital (A/D) converter 40'. The A/D converter is connected to a digital processor 41' which is connected to a readout box 36' (e.g., liquid crystal display). In a preferred embodiment the A/D converter, microprocessor and liquid crystal display driver circuitry are combined within a single chip (illustrated with dashed lines in FIG. 1) such as the $\mu$PD75328 chip available from NEC Electronics, Inc. The use of this single chip, which employs a 4-bit microprocessor with 8-bit A/D circuitry, with no loss of accuracy, greatly reduces the cost of production units. The linear voltage output (V) from detector 28' is data processed into a signal indicative of percent body fat which is then displayed on the readout box.

FIG. 2 illustrates use of an optical standard sleeve for "zero adjust" of the instrument by the user just before making readings. The standard is a near-infrared-opaque body or sleeve 70 having a cavity 162 and an internal flange 164 for cooperating with the end 165 of instrument 50. The dimensions are chosen such that the tip 166 of instrument 50 will be a predetermined distance (h) from the bottom portion of cavity 162. This distance is chosen to provide a reflectance value that corresponds to an interactance calibration value ($\%_{REF}$) for which the instrument is being calibrated (which is the function of the material's reflection properties and the geometry of the cavity). The standard reflects sufficient near-infrared radiation emitted from the near-infrared source in the probe to the near-infrared detectors present therein for "zeroing" or standardizing the probe for use in an interactance (measurement) mode. The sleeve 70 includes a reflective surface 72 (which reflects a known amount of near-IR radiation and, preferably reflects an amount of near-IR radiation which is substantially equal to the amount of near-IR radiation transmitted during near-IR interactance from a body of approximately 24% body fat content) at the standard distance (h) from the IREDs and detectors.

Figure 4:
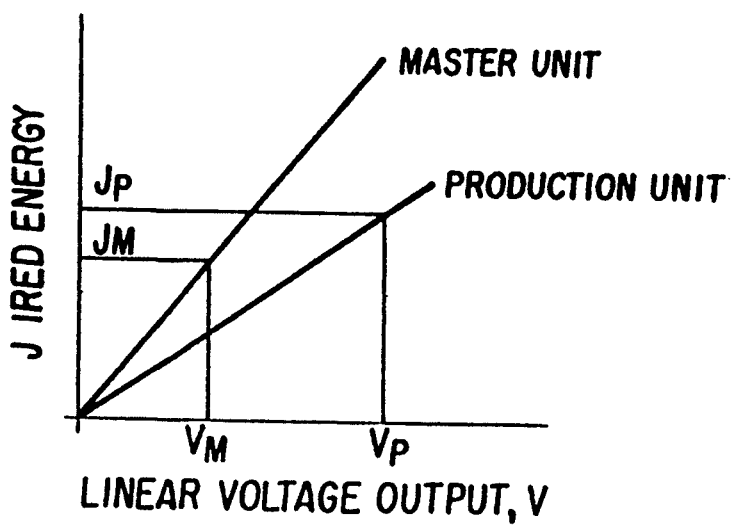
FIG. 4 is a plot of linear voltage output from an optical detector versus energy received from an IRED point source.

At the factory, a single "master unit" is calibrated using linear regression techniques in the conventional manner against a number of samples of known fat content (i.e., samples previously analyzed via another universally accepted technique such as underwater weighing). This calibration procedure provides values for the slope (hereinafter "$C_1$") and y-intercept (hereinafter "$C_o$") of the linear fat-determination equation which is used in the master and programmed into each production unit. In producing production units which are calibrated based upon the calibration of a single master unit, the following assumptions are made:

(1) The response of all of the linear detectors is linear with respect to light level, and zero voltage is output when light level is zero (see FIG. 4). Each detector has a different sensitivity (i.e. line slope), however, and this sensitivity can change as the detector ages. Thus, a zero adjust step, to calculate the detector line slope and store the value for use during interactance measurement, is to be performed by the user just prior to taking a measurement.

(2) The only difference from instrument to instrument is the difference in detector voltage output. This difference can be caused by differences in IRED energy, detector sensitivity, or power supply changes. There is no difference between units due to spectrum characteristics (because the IRED bandwidth is wide) or due to dimension changes.

(3) All optical standard sleeves provide identical reflective surfaces so that all sleeves will read the same value (within a few tenths of a percent) on a single instrument.

Following calibration against the known samples, the master unit is fitted with the optical standard sleeve and placed in the zero adjust mode. The readout will display the percent fat value associated with the optical standard according to the formula:

$$\%_{REF} = C_o + C_1 * V_M \quad (I)$$

where $V_M$ is the linear voltage output from the detector and $C_o$ and $C_1$ are intercept and detector line slope output values, respectively, known from the calibration of the master unit against the known samples. In order for a production unit to provide the same $\%_{REF}$ when the optical standard is measured in zero adjust mode, the following equation must be true:

$$\%_{REF} = K_o K_1 * V_P \quad (II)$$

where $K_o$ is an intercept value and $K_1$ is a detector line slope value as seen in FIG. 3. From FIG. 4 and equations I and II the following must be true:

$$\text{when } J_M = 0, \% = C_o \text{ (master unit)} \quad (III)$$

$$\text{when } J_P = 0, \% = K_o \text{ (production unit)} \quad (IV)$$

where J is voltage output from the respective detector. As it is desired to have the production units have the same calibration as the master unit, they also must read the same when their detectors output zero voltage. Thus, from (III) and (IV) above:

$$C_o = K_o \quad (V)$$

Thus, equation (II) becomes:
$$\%_{REF} = C_o K_1 * V_P \quad (VI)$$

Final zeroing of the production unit is to ensure that the unit behaves as closely as possible to the master unit and is carried out by the user in the following manner: The instrument 50 is put in "zero adjust mode" and is positioned within the standard sleeve 70 such that the tip 166 of the instrument 50 is spaced away from the bottom portion of cavity 162 so as to reflect sufficient near-infrared radiation emitted from the tip 166 back to the detector for calibrating the instrument for use in an interactance mode. When "zero adjust" is pressed on the production unit, the unit calculates $K_1$ from (VI) above and stores the $K_1$ value to use when measuring a person.

With only a single bandwidth measurement, a simple slope/bias computation is all that is required to directly determine percent fat. Thus when measuring a person, the equation is:

$$\% = C_o(\%_{REF} - C_o) \div V_P * V_{SUBJ}$$

where $C_o$, $V_P$ and $\%_{REF}$ are known from above, $V_{SUBJ}$ is the linear output from the detector when measuring the subject person and % is the person's body fat composition.

The material of the optical standard is chosen so that the reflectance characteristics makes it a usable standard for the constituent being measured, such as using polyvinyl chloride (PVC) for the calibration cup as a standard for fat and other types of measurements.

In operation, following calibration, the lower surface of the instrument is placed against the body for interactance measurement. Measurements of greatest accuracy are obtained when the instrument is placed against the biceps and oriented so that the line bisecting the IREDs runs perpendicular to the axis of the arm.

Elimination of the (log 1/I) calculation in favor of the disclosed 1/I based calculation has been shown to result in substantially no loss of accuracy in these interactance measurements. This is because the percent body fat function itself is essentially linear within the measured ranges. Calculations based on this linear function can advantageously be performed with lower cost data processing circuitry than that employed with logarithmic function calculations.

The elimination of costly factory calibration of each production unit in favor of user calibration via the simple zero adjust procedure taught herein also contributes to the lower cost of this preferred embodiment.

As noted above, the single measurement can be made using an IRED at almost any near-infrared center wavelength. However, people of African origin have flesh pigments that absorb light from the visible portion of the spectrum through the very near-infrared spectrum, disappearing at about 950 nanometers. Thus, the commercially available low-cost IREDs which provide a bandwidth output centering on 950 nanometers are practically ideal, since they avoid a substantial effect in the measurement based on skin color.

To provide even more accurate determination of percent body fat, data on a plurality of physical parameters of the body can be utilized along with the measured absorption of near-infrared radiation, to quantitatively determine the fat content of a body. Such physical parameters include, but are not limited to height, weight, exercise level, sex, race, waste-to-hip measurement, and arm circumference. When utilizing data on height and weight parameters in conjunction with measurement of near-infrared absorption in a single bandwidth measurement, a suitable equation is as follows:

$$\begin{aligned}\% \text{ body fat} &= K_o + (\%_{REF} - C_o)/V_P * V_{SUBJ} \\ &+ K_2 * W/100 * (1 - V_{SUBJ}/V_P) \\ &+ K_3 * H/100 * (1 - V_{SUBJ}/V_P)\end{aligned}$$

where values $K_2$ and $K_3$ are determined for the master unit by multiple linear regression analyses of known subjects as before, W is the subject's weight in pounds and height is his or her height in inches. Other parameters are similarly factored into the above equation.

The present invention provides a method and means for accurately and reliably measuring percent body fat, that is substantially less expensive than with previously known technology, and in a non-destructive manner, using near-infrared radiation interactance principles.

Since many modifications, variations and changes in detail may be made to the described embodiments, it is intended that all matter in the foregoing description and shown in the accompanying drawings be interpreted as illustrative and not in a limiting sense.

What is claimed is:

1. An apparatus for calibrating a probe for near-infrared interactance quantitative analysis, the calibrating apparatus comprising a near-infrared-opaque body, means defining a cavity in the body having a bottom portion with a predetermined geometrical shape, and means for positioning a near-infrared interactance light probe having a near-infrared source and detector within the cavity of the body with the bottom portion of the cavity spaced away from said source and said detector a distance that provides the bottom portion of the cavity with a reflectance value that corresponds to an interactance calibration value for which the probe is being calibrated, so as to reflect sufficient near-infrared radiation emitted from said source to said detector for calibrating the probe for use in an interactance mode.

2. A method for calibrating a near-infrared interactance probe for quantitative analysis of a material, comprising:
    (a) providing a near-infrared-opaque body having a cavity therein with a bottom portion having a predetermined geometrical shape;
    (b) positioning a near-infrared interactance probe, having a near-infrared source and detector, within the cavity of the body with the bottom portion of the cavity spaced away from said source and said detector a distance that provides the bottom portion of the cavity with a reflectance value that corresponds to an interactance calibration value for which the probe is being calibrated, so as to reflect sufficient near-infrared radiation emitted from such source to said detector for calibrating the probe for use in an interactance mode; and
    (c) calibrating the probe while positioned as in step (b).

* * * * *